US00PP08740P

United States Patent [19]

van Andel

[11] Patent Number: Plant 8,740

[45] Date of Patent: May 17, 1994

[54] ALSTROEMERIA NAMED STAMOLI

[75] Inventor: Jacob van Andel, Aalsmeer, Netherlands

[73] Assignee: Van Staaveren B.V., Aalsmeer, Netherlands

[21] Appl. No.: 31,397

[22] Filed: Mar. 11, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

*Attorney, Agent, or Firm*—Tilton, Fallon, Lungmus & Chestnut

[57] ABSTRACT

A new and distinctive Alstroemeria cultivar particularly distinguished by its profuse and recurrent production of very large flowers, having six petals arranged in two concentric circles of three petals per flower. The outer petal being chrome red with an orchard pink base. The inner petals being white with an orchard pink base and many chrysanthemum crimson stripes.

1 Drawing Sheet

BACKGROUND OF THE NEW PLANT

This Alstroemeria cultivar originated as a sport of a hybrid, from the parent variety 'Stablaco' (U.S. Plant Pat. No. 4,930) and was produced in my nursery at Aalsmeer, The Netherlands. The plant, hereinafter described, was selected from a planting of the parent variety maintained at my nursery for breeding purposes. 'Stablaco' is known in commerce under the synonym 'Mona Lisa'. This particular sport was selected because of its short stem which makes it suitable as a pot type Alstroemeria. This new plant most closely resembles the parent, commercial variety 'Stablaco'. 'Stamoli' differs from 'Stablaco' in that 'Stamoli' is much shorter than 'Stablaco'; 'Stamoli' attaining only 49–60 cm in height whereas 'Stablaco' is about 200 cm in height. 'Stamoli ' has white petals like 'Stablaco', however, 'Stamoli' has crimson colored stripes whereas 'Stablaco' has brown colored stripes. The short height of 'Stamoli' is a result of genetic change. The difference in color between the claimed cultivar and 'Stablaco', is a result of the difference in growing conditions. 'Stablaco' is grown under controlled greenhouse conditions whereas 'Stamoli' is grown outdoors.

Another difference between 'Stamoli' and 'Stablaco' is that the color of the petals of 'Stamoli' when the petals first being to unfurl is RHS 40. The color of the petals of 'Stablaco', when they first being to unfurl, is RHS 158 C-D. Also, 'Stamoli' has one pistil and 'Stablaco' has three. The color of the pollen of 'Stamoli' is yellow-green whereas for 'Stablaco' the pollen is grey/-green in color. 'Stablaco' is characterized by its unusual, almost pure white flowers highlighted by the upper petals which have brown pencil stripe streaks extending over a yellow background from a pink throat or base.

This selected sport was propagated by me at Aalsameer, The Netherlands, by dividing root stock with very satisfactory results and thereafter this selected plant was propagated through several successive generations in the same manner which demonstrated conclusively that the novel characteristics of the originally selected sport would be maintained from generation to generation and its homogeneity would be firmly established.

DESCRIPTION OF THE DRAWING

My new Alstroemeria plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new Alstroemeria plant as observed from plants grown under greenhouse conditions in Aalsmeer, The Netherlands, with the stated flower colors being according to The R.H.S. Colour Chart of The Royal Horticultural Society of London, England.

THE PLANT

Origin: Sport (spontaneous mutant).

Parentage: 'Stablaco' U.S. Plant Pat. No. 4930. The parent plant is so identified in my business records of my nursery maintained at the offices in Aalsmeer, The Netherlands. The aforementioned sport are also recorded therein.

Classification:

*Botanic.*—Alstroemeria hybrid.

*Commercial.*—Alstroemeria hybrid.

Form: An upright bush.

Height: About 49–60 cm.

Growth rate: Flowering in about 3–5 months following the first planting.

Main stem length: 50 cm.

Strength: Strong.

Branching character: The main stem has an umbel in which 3–5 branches (peduncles) are grouped. At the end of the peduncle a flower is situated on a pedicel. Above the peduncle additional pedicels may occur. The number of flowers per branch is 1–2.

Growth: Vigorous.

Foliage:

*Quantity.*—Abundant.

*Number of leaves.*—20–25.

*Size and shape of leaf.*—The leaf is elliptical shaped, about 10–14 cm in length and about 2–2.5 cm in width.

*Margin type.*—Smooth.

*Texture.*—Smooth.

*Color.*—Upper side — 143 A. Under side — 143B.

Rhizomes: Yes.

*Color.*—RHS 155D.

*Size.*—10–15cm.

THE BUD

Size:

*Diameter.*—1 cm.

*Length.*—2 cm.

Shape: Pear-shaped.

Rate of opening: Bud to flower in about 3–5 days.

Color of petals:

*When sepals first divide.*—RHS 4D.

*When petals begin to unfurl.*—RHS4D.

Splitting: No.

THE FLOWER

Blooming habit: Intermittent and profuse- Spring and Fall.

Size of bloom: Medium.

*Diameter.*—5–6 cm.

*Depth.*—4–5 cm.

Borne: Singly.

Shape: When bloom first opens and when it matures the blooms are cup shaped.

Petalage:

*Number of petals.*—Six.

*Arrangement.*—Two concentric circles of three petals.

*Texture.*—Minutely crinkled or creped.

*Form.*—The three outer petals are lobed at the apex and the three inner petals are lanceolate to obovate in shape.

*Margin type.*—Very finely dentate along the entire margin.

*Apex.*—Pointed.

*Appearance.*—Shiny.

*Remain on stem.*—Two weeks.

*Color.*—Outer petals Body: RHS 158C/D Base:RHS 62C. Reverse Side: RHS 158CD/62B.

Inside petals The body of the top two inner petals are RHS 158 C/D in color with shadings of RHS 5-B. The base is RHS 62-D in color. The body of the third inner petal is RHS 158 C/D and the base is RHS 62 D. The stripes are combined to the inner petals and are RHS 59 B in color. Base:RHS 62D. Reverse side RHS 158C/D/62B. Stripes: 20–30. Color: RHS 185A.

Discoloration after full bloom: Slightly.

Persistence: The petals of matured flowers do not hang on and dry.

Fragrance: None.

Lasting quality:

*On the plant.*—About 3 weeks

*As a cut flower.*—About 2 weeks.

Flower stem:

*Length.*—About 2–3 cm.

*Character.*—Upright and strong.

*Color.*—RHS 143A.

THE REPRODUCTIVE ORGANS

Stamens:

*Number.*—About six.

*Arrangement.*—Clustered around the style.

*Anthers.*—Size: 8–10 mm. Color: RHS 148A.

*Filaments.*—Length: About 5 cm. Color: RHS 62A.

*Pollen.*—Color: RHS 152A.

Pistils:

*Number.*—One.

*Styles.*—Length about 4–5 cm (RHS 62C)

*Stigmas.*—RHS 62A.

Fruit:

*Fertile.*—No.

*Shape.*—Round.

I claim:

1. A new and distinctive Alstroemeria plant, substantially as herein shown and described.

* * * * *

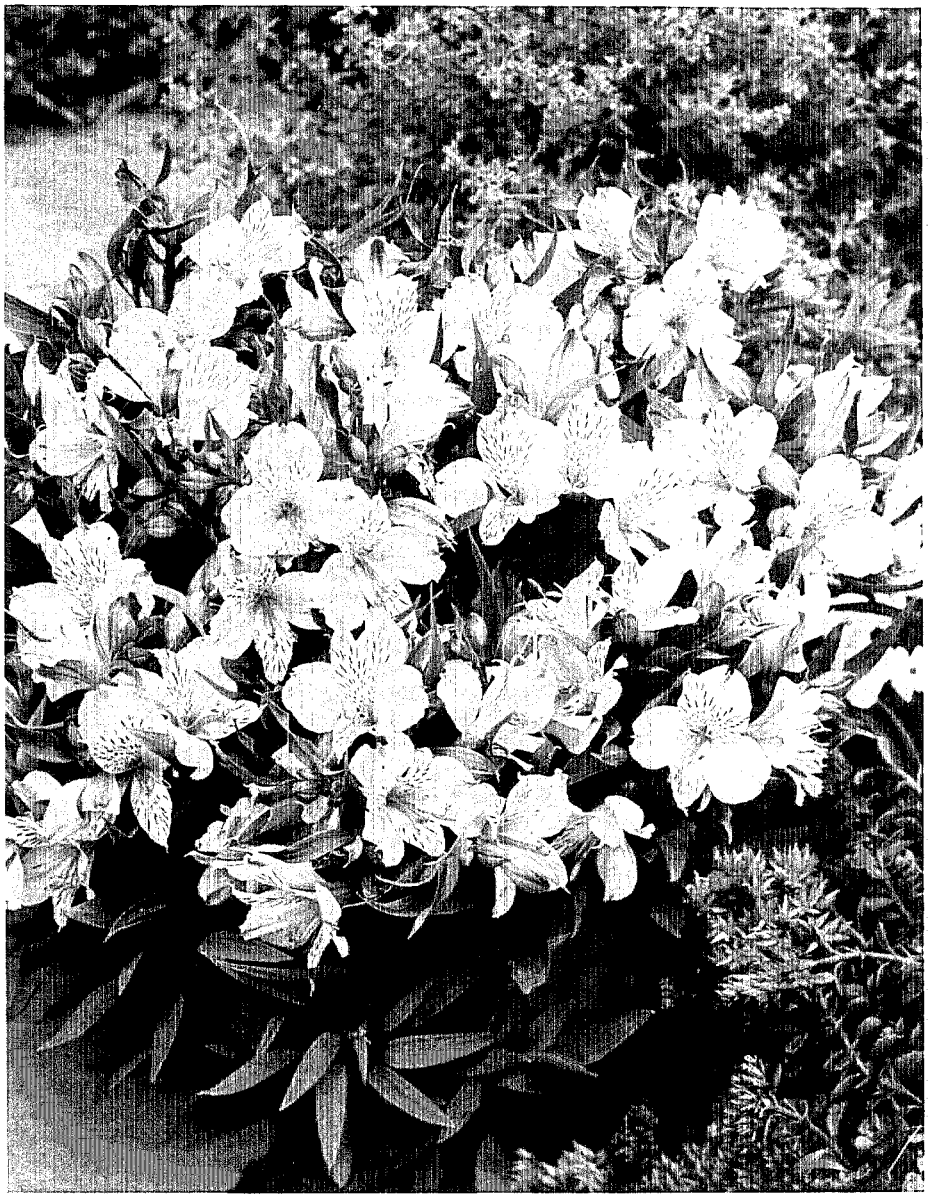

UNITED STATES PATENT AND TRADEMARK OFFICE

CERTIFICATE OF CORRECTION

PATENT NO. : PP 8,740

DATED : May 17, 1994

INVENTOR(S) : Jacob van Andel

It is certified that error appears in the above-indentified patent and that said Letters Patent is hereby corrected as shown below:

Title page, item [57], col. 2,

In the Abstract, line 5, delete "chrome red" and insert -- white --.

In column 2, line 30, delete "5" and insert --4 --.

Signed and Sealed this

Eleventh Day of October, 1994

Bruce Lehman

*Attest:*

BRUCE LEHMAN

*Attesting Officer*

*Commissioner of Patents and Trademarks*